United States Patent
Fujii et al.

(10) Patent No.: US 6,329,410 B1
(45) Date of Patent: Dec. 11, 2001

(54) WATER-BASE LIQUID PREPARATION

(75) Inventors: Tsuneo Fujii; Toshihiro Baba, both of Fukuoka (JP)

(73) Assignees: Welfide Corporation, Osaka; SPP Co., Ltd., Tokyo, both of (JP)

( * ) Notice: Subject to any disclaimer, the term of this patent is extended or adjusted under 35 U.S.C. 154(b) by 0 days.

(21) Appl. No.: 09/582,291

(22) PCT Filed: Dec. 21, 1998

(86) PCT No.: PCT/JP98/05781

§ 371 Date: Jun. 23, 2000

§ 102(e) Date: Jun. 23, 2000

(87) PCT Pub. No.: WO99/33464

PCT Pub. Date: Jul. 8, 1999

(30) Foreign Application Priority Data

Dec. 25, 1997 (JP) .................................. 9-357608

(51) Int. Cl.[7] ...................................... A61K 31/41
(52) U.S. Cl. ............................................. 514/383
(58) Field of Search ................................. 514/383

(56) References Cited

U.S. PATENT DOCUMENTS 5,147,886 * 9/1992 Tokizawa et al. ................... 514/383

FOREIGN PATENT DOCUMENTS 3-223266   10/1991  (JP) ............................ C07D/249/08
9-227531    9/1997  (JP) ............................ C07D/249/08

OTHER PUBLICATIONS

Carl J. Lintner, Ph.D. "Stability of Pharmaceutical Products"Remington's Pharmaceutical Sciences, 16, pp. 1425–1429 (1980).

* cited by examiner

Primary Examiner—Theodore J. Criares
Assistant Examiner—Jennifer Kim
(74) Attorney, Agent, or Firm—Sughrue, Mion, Zinn, Macpeak & Seas, PLLC

(57) ABSTRACT

An aqueous liquid preparation, which has a pH of from 3 to 5 and comprises (R)-(−)-3-methyl-3-methyl-sulfonyl-1-(1H-1,2,4-triazol-1-yl)-2-[4-(trifluoromethyl)phenyl]butan-2-ol or a pharmaceutically acceptable salt thereof; and an injection for intravenous administration comprising the aqueous liquid preparation.

1 Claim, No Drawings

WATER-BASE LIQUID PREPARATION

TECHNICAL FIELD

The present invention relates to an aqueous liquid preparation suitable for intravenous injection, comprising (R)-(−)-3-methyl-3-methylsulfonyl-1-(1H-1,2,4-triazol-1-yl)-2-[4-(trifluoromethyl)phenyl]butan-2-ol having an excellent antifungal effect, or a pharmaceutically acceptable salt thereof.

BACKGROUND ART

Mycoses involve skin diseases typified by various trichophytoses, leprid, psoriasis, cutaneous candidiasis, and the like, and deep mycoses typified by mycotic meningitis, mycotic respiratory infection, hematomycosis, mycosis of urinary tract, and the like.

Among these, deep mycoses cannot be treated by using a usual antibiotic or chemotherapeutic agent, and thus the number of patients suffering therefrom shows a tendency to rise. Accordingly, there have been required drugs efficacious in treating them.

At present, only four drugs are clinically usable in treating deep mycoses, namely, amphotericin B which is a peptide antibiotic, flucytosine which is a growth inhibitor for fungal cells, and fluconazole and itraconazole which are azole antifungal agents. However, these agents are not satisfactory yet. Moreover, it is said that deep mycoses would frequently cause multiple fungal infection. Thus, it has been required to develop a drug having a broader antifungal spectrum. Under these circumstances, a triazole derivative, (R)-(−)-3-methyl-3-methylsulfonyl-1-(1H-1,2,4-triazol-1-yl)-2-[4-(trifluoromethyl)phenyl]butan-2-ol, and pharmaceutically acceptable salts thereof have been found (JP-A-3-223266 and JP-A-7-2802). This compound will be sometimes referred to as "the present compound" in this description.

The present compound has excellent characteristics of: (1) showing an antifungal effect on the genus Aspergillus in addition to the genera Candida and Cryptococcus; (2) showing an antifungal effect even on the genus Candida which is fluconazole-resistant; (3) showing an excellent therapeutic effect on a neutropenia systemic fungal infection model (in vivo); (4) causing a more remarkable decrease in the viable count in the lung in a local infection model (in vivo) than existing drugs; (5) having a higher selectivity of P450 derived from fungi and animals than existing drugs; (6) having a water solubility which is usable as injections; and (7) having a safety margin comparable to existing drugs. Thus, it is expected that it is useful as a remedy for deep mycoses.

The present compound has a water solubility which is usable as injections. Therefore, it is preferred that the present compound is used as injections from the viewpoint of providing dosage forms over a wide range, in particular, those for intravenous administration.

Although the antifungal effect of the present compound was proved by orally administering it to mice in JP-A-3-223226, it is disclosed that the compound can be formulated by conventional methods into antifungal agents in various dosage forms, such as tablets, granules, powders, capsules, suspensions, injections, suppositories, external preparations, and the like. When injections are prepared, it is also disclosed that the present compound may be preliminarily dissolved, dispersed, emulsified, etc. in an aqueous carrier, such as distilled water for injection or the like, or formulated into powders for injection which are to be dissolved when they are used, namely, the present compound is usable as injections by conventional methods.

In order to prepare an injection for intravenous administration, it is necessary to add an isotonizing agent (an osmotic regulator) to regulate the osmotic pressure of the aqueous solution. Thus, the present inventors prepared an injection by using sodium chloride (0.9 W/V %) commonly used as an isotonizing agent. As a result, they have found that the present compound is decomposed at a considerably high ratio by heat sterilization and that its decomposition product is increased when stored over a long time. To develop an injection, it is necessary to minimize the decomposition during heating and enhance the stability. However, no such injection has been obtained so far.

DISCLOSURE OF THE INVENTION

Accordingly, an object of the present invention is to provide an aqueous liquid preparation of the present compound keeping an osmotic pressure suitable for intravenous administration, being prevented from thermal decomposition during sterilization as far as possible, having a high storage stability and thus being suitable for intravenous injection, and to injections for intravenous administration using the same.

As a result of intensive studies, the present inventors have found that when an aqueous solution of the present compound is adjusted to a specific pH value, the decomposition product formed by heat sterilization can be reduced, no decomposition product is formed after the sterilization and it is stable with the passage of time. Thus, the present invention has been completed.

Accordingly, the present invention provides an aqueous liquid preparation, which has a pH of from 3 to 5 and comprises (R)-(−)-3-methyl-3-methylsulfonyl-1-(1H-1,2,4-triazol-1-yl)-2-[4-(trifluoromethyl)phenyl]butan-2-ol having a broad antifungal spectrum, or a pharmaceutically acceptable salt thereof.

BEST MODE FOR CARRYING OUT THE INVENTION (R)-(−)-3-Methyl-3-methylsulfonyl-1-(1H-1,2,4-triazol-1-yl)-2-[4-(trifluoromethyl)phenyl]butan-2-ol or a pharmaceutically acceptable salt thereof, which is an active ingredient of the aqueous liquid preparation of the present invention, can be produced by, for example, the methods described in JP-A-3-223266 and JP-A-7-2802.

Examples of the pharmaceutically acceptable salt include hydrochloride, nitrate, hydrobromide, sulfate, p-toluenesulfonate, methanesulfonate, fumarate, maleate, succinate, lactate, bromocamphorsulfonate, and the like.

The aqueous liquid preparation of the present invention can be stabilized by regulating the pH to 3 to 5. Examples of a pH regulator for adjusting the pH to 3 to 5 include anhydrous sodium monohydrogenphosphate, citric acid, sodium citrate, hydrochloric acid, lactic acid, sodium hydroxide, dry sodium carbonate, dilute hydrochloric acid, crystalline sodium dihydrogenphosphate, succinic acid, acetic acid, sodium acetate, tartaric acid, sodium hydrogencarbonate, sodium carbonate, triethanolamine, sodium lactate solution, glacial acetic acid, citric anhydride, anhydrous sodium dihydrogenphosphate, meglumine, monoethanolamine, phosphoric acid, trisodium phosphate, sodium hydrogenphosphate, dipotassium phosphate, potassium dihydrogenphosphate, sodium dihydrogenphosphate, and the like. They may be used alone or a combination thereof to adjust the pH to 3 to 5.

These pH regulators may be used in an effective and pharmaceutically acceptable amount. For example, anhydrous sodium monohydrogenphosphate is used at an amount of from 0.1 to 8.0 parts by weight per part by weight of the present compound.

The aqueous liquid preparation of the present invention has preferably a pH of form 3 to 5, more preferably form 3 to 4.5. The stabilizing effect according to the present invention can be effectively achieved within this range. A preparation having a pH value less than 3 is not favorable as an injection due to that it shows a tendency to give a strengthened local stimulus (rash pain) when an injection needle sticks in the body.

In order to prepare an injection for intravenous administration, it is also necessary to add an isotonizing agent (an osmotic regulator). Examples of the isotonizing agent appropriate for the aqueous liquid preparation of the present invention include one or at least two of substances selected from phosphates (phosphoric acid, sodium hydrogenphosphate, disodium hydrogenphosphate, potassium dihydrogenphosphate, anhydrous sodium pyrophosphate, crystalline sodium dihydrogenphosphate, calcium hydrogenphosphate, etc.), saccharides (glucose, D-mannitol, D-sorbitol, lactose, fructose, sucrose, etc.), polyols (glycerol, xylitol, MACROGOL 4000™, etc.), sulfates (sodium hydrogensulfite, etc.), chlorides (potassium chloride, sodium chloride, magnesium chloride, calcium chloride, etc.), bromides (sodium bromide, calcium bromide, etc.), hydroxides (sodium hydroxide, etc.), carbonates (sodium hydrogencarbonate, etc.) and others (nicotinic acid amide, propylene glycol, benzyl alcohol, aminoethylsulfonic acid, benzalkonium chloride, sodium lactate, etc.). Among these, it is preferred to use saccharides, such as glucose, D-mannitol, D-sorbitol, and the like, and glucose is particularly preferred. It is usually preferred to use from 10 to 300 parts by weight of the isotonizing agent per part by weight of the present compound.

When the isotonizing agent is selected from sulfates, chlorides, bromides, hydroxides, carbonates and others, such as nicotinic acid amide, propylene glycol, benzyl alcohol, aminoethylsulfonic acid, benzalkonium chloride, sodium lactate, and the like, among the above isotonizing agents, it is preferred to adjust the pH of the aqueous liquid preparation to about 3 to 4.5.

The concentration of the present compound in the aqueous liquid preparation is usually from 0.01 to 0.07 W/V %. Examples of water to be used as a solvent include distilled water for injection, sterilized purified water, and the like.

The injection of the present invention can be produced by dissolving the present compound and the isotonizing agent in distilled water for injection, etc., further optionally adding and dissolving additives for injection, such as a preservative, a soothing agent, or the like, adjusting the pH to 3 to 5 with the pH regulator, then filtering the resultant mixture according to a conventional method, such as a membrane filter, and filling the filtrate into a vial or a transfusion bottle. Subsequently, the vial or the bottle is stopped with a rubber stopper for exclusive use and rolled with a flip-off cap or an aluminum seal, followed by steam sterilization (for example, at 100 to 130° C. for about 20 to 40 minutes) to give a final product having a good storage stability.

Examples of the above-described preservative include quaternary ammonium salts, such as benzalkonium chloride and the like; parabens, such as methyl parahydroxybenzoate, ethyl parahydroxybenzoate, and the like; sorbic acid; and the like. Examples of the above-described soothing agent include benzyl alcohol, propylene glycol, sodium hydrogencarbonate, magnesium sulfate, and the like.

The aqueous liquid preparation of the present invention is usable as, for example, an injection for intravenous administration in treating deep mycoses (hematomycosis, mycotic respiratory infectious diseases, mycotic meningitis, digestive mycosis, urologic mycosis) and superfacial mycoses (oral candidiasis, cutaneous candidiasis, trichophytosis) caused by fungi belonging to the genera Candida, Cryptococcus and Aspergillus, and the like.

When the aqueous liquid preparation of the present invention is used in treating a deep mycosis in the form of an injection, it is used in a single dose, expressed in terms of the present compound, of 10 to 100 mg and administered to an adult in a daily dose of 10 to 300 mg, preferably 10 to 100 mg, once or several times.

The present invention will be described in greater detail by reference to the following Experimental Examples and Examples. However, it is to be understood that the present invention is not construed as being limited thereto.

Experimental Example 1

Discussion on Isotonizing Agent

In 100 ml of distilled water, 50 mg of the present compound was dissolved, and 0.9 to 5 g of an isotonizing agent was added thereto and dissolved, and the resultant mixture was packed in a vial (pH 6 to 7). Then it was sterilized by heating at 115° C. for 30 minutes or at 100° C. for 30 minutes (twice). The content of the heat decomposition product in the solution was measured using high performance liquid chromatography, and the amount of the heat decomposition product formed after the sterilization was calculated.

Table 1 shows the amounts of the heat decomposition product formed using D-mannitol, glucose or sodium chloride (common salt) as the isotonizing agent.

TABLE 1

| Isotonizing agent | Heat decomposition product formed (%) | |
|---|---|---|
| | 115° C., 30 min | 100° C., 30 min (twice) |
| None | 4.6 | 1.2 |
| 5% D-Mannitol | 0.6 | 0.2 |
| 5% Glucose | 0.1 | 0.1 |
| 0.9% Sodium chloride | 2.1 | 0.3 |

As apparent from Table 1, the amount of the heat decomposition product was reduced by adding the isotonizing agent. In particular, the addition of glucose caused a large decrease in the amount of the heat decomposition product. However, the heat decomposition product was still formed, and thus these samples were insufficient in storage stability too.

Experimental Example 2

Effect of pH

In 100 ml of distilled water, 50 mg of the present compound was dissolved, and 5 g of glucose or 0.9 g of sodium chloride was added thereto as an isotonizing agent. After dissolving, solutions of pH 3, 4, 4.5 and 5 were prepared using anhydrous sodium monohydrogenphosphate and citric acid as pH regulators. The obtained solutions were each filtered, packed in a vial and then sterilized by heating at 115° C. for 30 minutes. The samples containing sodium chloride were sterilized at 121° C. for 20 minutes. The content of the heat decomposition product of the present compound was measured using high performance liquid chromatography, and thus the amount of the heat decomposition product formed after the sterilization was calculated. Table 2 shows the results.

TABLE 2

| | Heat decomposition product formed (%) | |
|---|---|---|
| pH | Glucose, 115° C., 30 min | Sodium chloride, 121° C., 20 min |
| 5 | <0.1 | 1.8 |
| 4.5 | not detected | <0.1 |
| 4 | not detected | not detected |
| 3 | not detected | not detected |

As apparent from Table 2, the samples containing glucose showed little formation (1% or less) of the decomposition product after the sterilization at pH 5 and no formation of the decomposition product at pH 3, 4 and 4.5. In the samples containing sodium chloride, the formation of the decomposition product after the sterilization was regulated to 1.8% and 0.1% or less respectively at pH 5 and 4.5. Furthermore, no formation of the decomposition product was observed at pH 3 and 4. Accordingly, it has been confirmed that the pH of from 3 to 4.5 is particularly preferred. Both of the samples containing glucose and sodium chloride remained stable with the passage of time, when adjusted to a pH of 3 to 5.

Experimental Example 3

Solutions (pH 4) prepared as in Experimental Example 2, except for using 1.5 to 3% of isotonizing agents other than glucose or sodium chloride, were sterilized by heating at 115° C. for 30 minutes. Then the content of the heat decomposition product of the present compound in each solution was measured using high performance liquid chromatography, and thus the amount of the heat decomposition product formed after the sterilization was calculated. Table 3 shows the results.

TABLE 3

| Isotonizing agent | Heat decomposition product formed (%) |
|---|---|
| Glycerol | not detected |
| Sodium hydrogensulfite | not detected |
| Potassium chloride | <0.1 |
| Magnesium chloride | <0.1 |
| Sodium bromide | <0.1 |
| Propylene glycol | not detected |
| Sodium lactate solution | <0.1 |

Each isotonizing agent showed an excellent stabilizing effect.

EXAMPLE 1

In distilled water for injection, 500 mg of the present compound, 50 g of glucose, 100 mg of anhydrous sodium monohydrogenphosphate and an adequate amount of citric acid were dissolved, and the total volume was adjusted to 1,000 ml. The pH of the solution was adjusted to 3.5 to 4.5 by adding anhydrous sodium monohydrogenphosphate or citric acid thereto. The obtained solution was filtered and packed in a 100 ml vial, followed by stopping with a rubber stopper and rolling with an aluminum seal. After sterilizing at 115° C. for 30 minutes, an injection containing 50 mg of the present compound per vial was obtained (final pH: 4.27).

EXAMPLE 2

An injection containing 50 mg of the present compound per vial was obtained in the same manner as in Example 1 using the following components, except for sterilizing at 121° C. for 20 minutes (final pH: 4.01).

| | |
|---|---|
| Present compound | 500 mg |
| D-mannitol | 50.0 g |
| Anhydrous sodium monohydrogenphosphate | 100.0 mg |
| Citric acid | q.s. (pH 4) |
| Distilled water for injection | q.s. |
| Total | 1,000 ml. |

EXAMPLE 3

An injection containing 50 mg of the present compound per vial was obtained in the same manner as in Example 1 using the following components, except for sterilizing at 121° C. for 20 minutes (final pH: 3.90).

| | |
|---|---|
| Present compound | 500 mg |
| Sodium chloride | 9.0 g |
| Anhydrous sodium monohydrogenphosphate | 100.0 mg |
| Citric acid | q.s. (pH 3 to 4) |
| Distilled water for injection | q.s. |
| Total | 1,000 ml. |

Experimental Example 4

Stability Test

The stability (40° C., 6 months) of the vialed injection obtained in Example 1 was examined. Table 4 shows the results.

TABLE 4

| Storage time | Appearance | Content (%) of active ingredient | Decomposition product formed (%) | Final pH |
|---|---|---|---|---|
| Starting | Colorless, transparent | 100.0 | ≦0.1 | 4.27 |
| 2 months | Colorless, transparent | 100.7 | ≦0.1 | 4.29 |
| 4 months | Colorless, transparent | 99.8 | ≦0.1 | 4.06 |
| 6 months | Colorless, transparent | 100.6 | ≦0.1 | 4.05 |

Thus, the injection according to the present invention remains highly stable after storing at 40° C. for 6 months.

Industrial Applicability

The present invention provides an aqueous liquid preparation, particularly an injections suitable for intravenous administration, of the present compound which forms little decomposition product even by heat sterilization and has excellent storage stability. The injection of the present invention is usable in treating deep mycoses (hematomycosis, mycotic respiratory infectious diseases, mycotic meningitis, digestive mycosis, urologic mycosis) and superfacial mycoses (oral candidiasis, cutaneous candidiasis, trichophytosis) caused by fungi belonging to the genera Candida, Cryptococcus and Aspergillus, and the like.

What is claimed is:

1. An injection to be heat sterilized for intravenous administration, comprises an aqueous liquid preparation comprising (R)-(−)-3-methyl-3-methyl-sulfonyl-1-(1H-1,2,4-triazol-1-yl)-2-butan-2-ol or a pharmaceutically acceptable salt thereof, and an isotonizing agent, whereby the amount of heat decomposition product formed upon heat sterilization is <0.1% which has a pH from 3 to 4.5.

* * * * *